United States Patent [19]
Schmidt et al.

[11] Patent Number: 4,681,413
[45] Date of Patent: Jul. 21, 1987

[54] HEADBAND WITH OPTICAL DEVICE ADJUSTABLY COUPLED THERETO

[75] Inventors: Otto H. Schmidt; Helmut A. Heine, both of Herrsching; Helmut Rosenbusch, Weilheim, all of Fed. Rep. of Germany

[73] Assignees: Propper Manufacturing Co., Inc., Long Island City, N.Y.; Heine Optotecnik GmbH & Co. KG, Herrsching, Fed. Rep. of Germany

[21] Appl. No.: 698,362

[22] Filed: Feb. 5, 1985

[51] Int. Cl.⁴ ............................................. A61B 3/10
[52] U.S. Cl. ................................. 351/205; 351/156
[58] Field of Search .............. 351/205, 214, 155, 156, 351/58, 59, 60, 47; 2/6

[56] References Cited
U.S. PATENT DOCUMENTS

| | | | |
|---|---|---|---|
| 2,158,642 | 9/1936 | Tartrais | 351/156 |
| 3,548,411 | 12/1970 | Barstow et al. | 351/47 |
| 4,538,888 | 9/1985 | Sigelman | 351/205 |

*Primary Examiner*—Rodney B. Bovernick
*Assistant Examiner*—P. M. Dzierzynski

*Attorney, Agent, or Firm*—Amster, Rothstein & Ebenstein

[57] ABSTRACT

Head-worn apparatus to which an optical device is adjustably coupled is disclosed. The apparatus comprises a headband, a support bow for the optical device rotatably coupled to the headband and a locking mechanism for automatically locking the bow in a viewing position of the optical device and in a rest position of the optical device while permitting the bow to be swivelled between the two positions. An articulated coupling adjustably connects the optical device to the central region of the bow. The locking mechanism always locks the bow in the same viewing position of the optical device so that once the articulated coupling has been adjusted with the optical device in its viewing position, the bow and with it the optical device can be swivelled back and forth between the rest and use positions without having to readjust the optical device. This arrangement enables a user to position an optical device in front of his or her eyes for use and move it out of the way without either taking the apparatus off his or her head or readjusting the optical unit.

33 Claims, 13 Drawing Figures

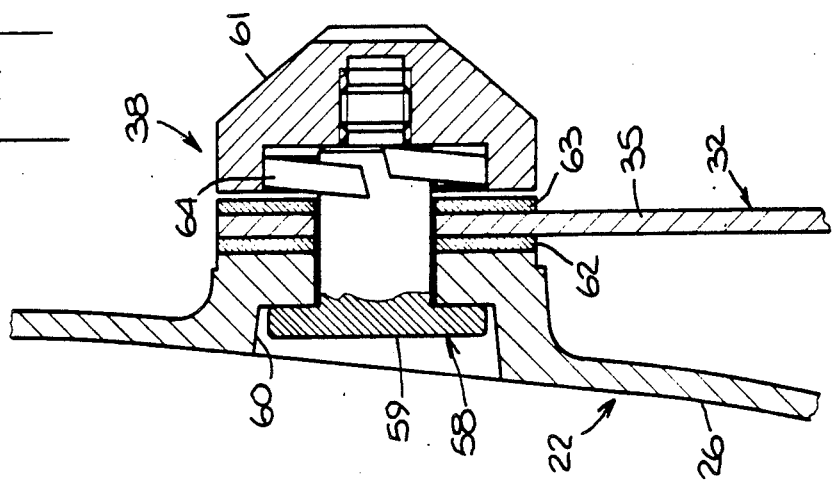
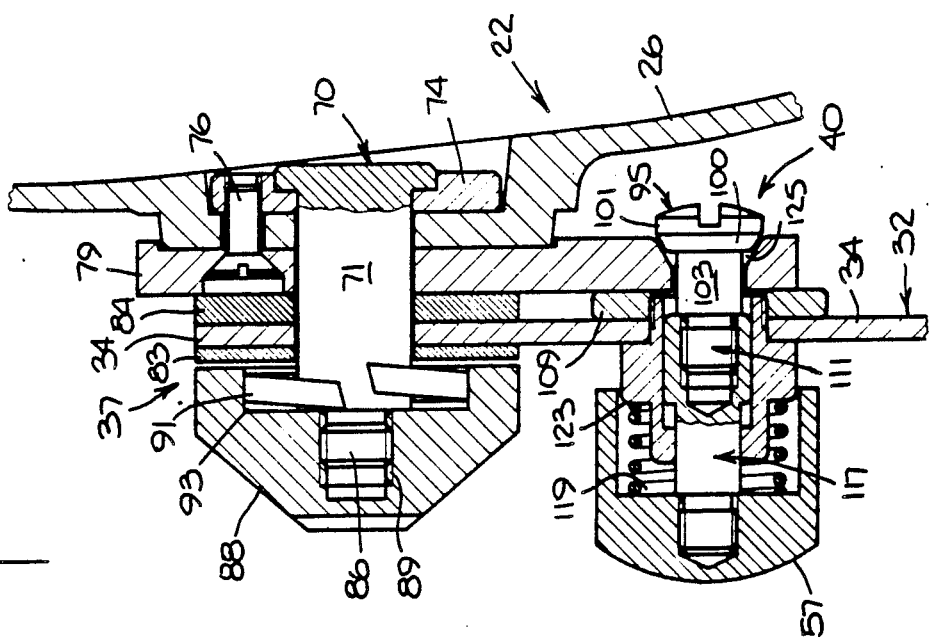

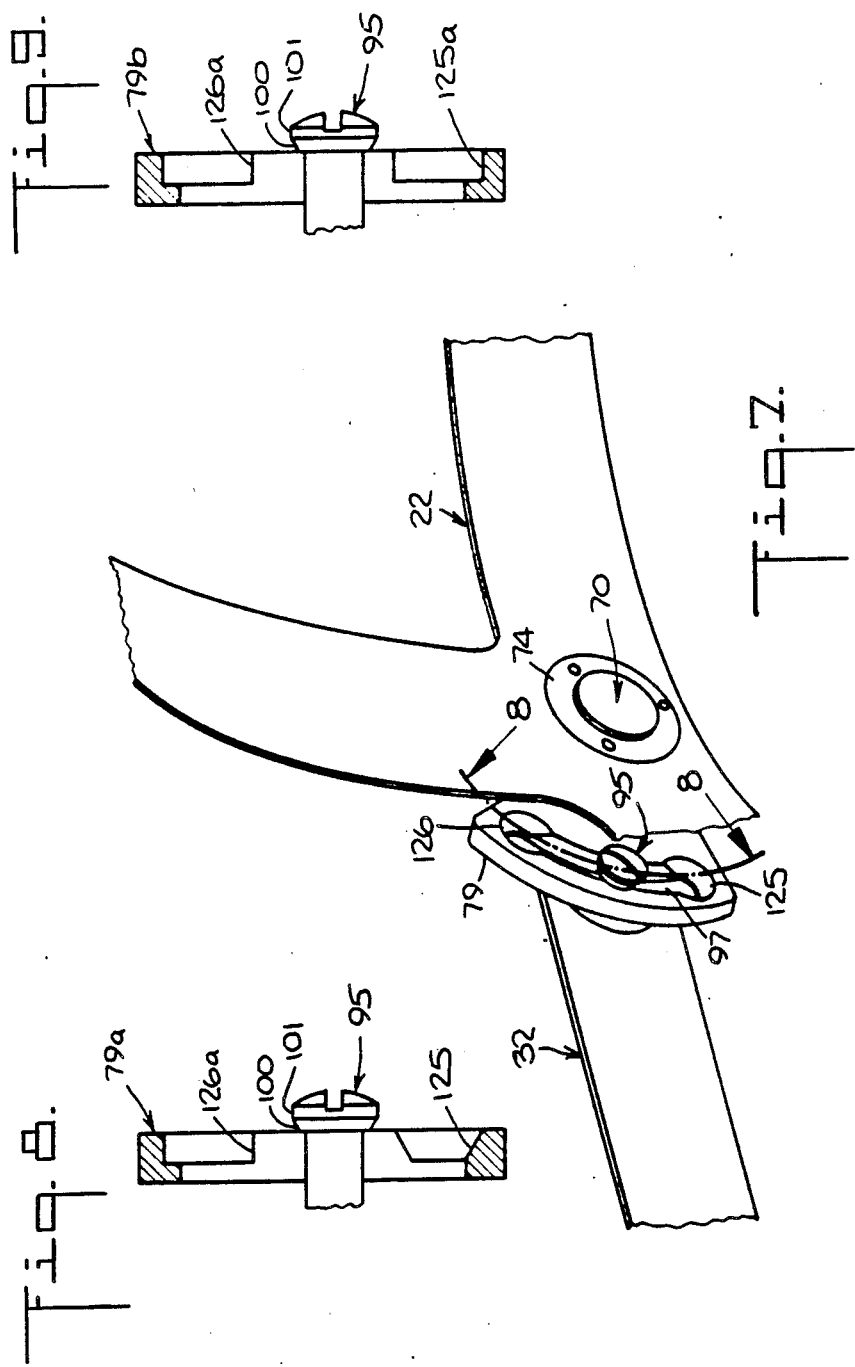

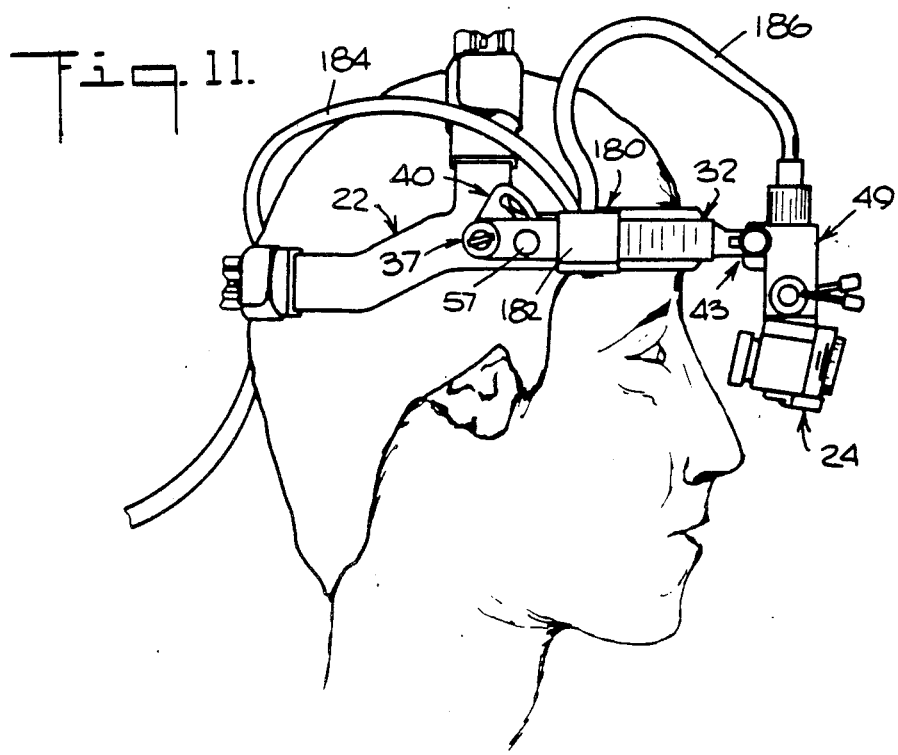
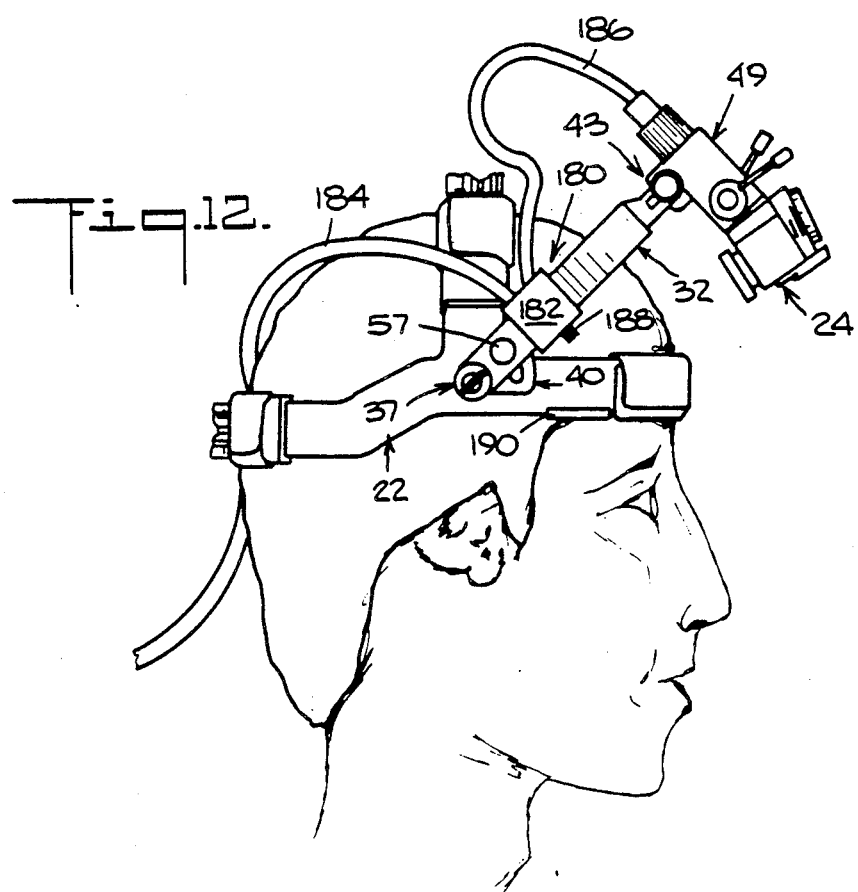

HEADBAND WITH OPTICAL DEVICE ADJUSTABLY COUPLED THERETO

BACKGROUND OF THE INVENTION

The present invention relates to head-worn apparatus including an optical device adjustably coupled thereto, and to coupling apparatus for adjustably securing the optical device.

Head-worn binocular ophthalmoscopes essentially include two components, an optical unit and a headband. A known headband comprises a lower, annular band enclosing the top of the head and an upper, semi-circular band laterally connected thereto. Both bands are flexible and may be made of plastic, and can be adjusted to the size and shape of the examiner's head by means of adjusting devices. The optical unit is attached directly to the front side of the lower band by an adjustable coupling device which permits the examiner to adjust the height, distance and inclination of the optical unit in relation to his or her eyes, so as to optimally position the optical device relative to the examiner's eyes. However, the headband is typically removed by the examiner when the optical unit is not being used and the examiner wishes to completely clear his or her field of view, even during the course of an examination.

In another head-worn binocular ophthalmoscope, the optical unit is not attached directly to the headband, but to an approximately semi-circular metal bow by means of an adjusting device. The sides of the bow are pivotally attached to the headband so the bow can be laterally pivoted on the headband. The pivoting arrangement for each side of the bow includes a rotatable knob, each of which must be tightened to lock the bow and loosened to move the bow. The bow is thus capable of being pivoted on the headband and locked in a pivoted position by the knobs. To use the optical unit, the bow is lowered and locked by the knobs in a viewing position of the optical unit and the optical unit is adjusted relative to the bow for optimal viewing. When the examiner wishes to move the optical unit out of his or her field of view, the bow is unlocked, swung upwardly completely out of the examiner's field of view and locked again. This arrangement has the advantage that the examiner does not have to take the headband off while pausing during an examination and then replace it in order to continue with the examination. A disadvantage, however, with this headband arrangement is that the knobs must be loosened and tightened for each upward and downward swivelling of the bow with attached optical unit in order to move it from one position to another, and the bow and/or the adjusting device has to be readjusted to exactly position the optical unit in the viewing position each time the bow is swivelled, so as to provide the examiner with optimal viewing conditions.

OBJECT AND SUMMARY OF THE INVENTION

It is an object of the present invention to provide head-worn apparatus including an optical device which avoids the disadvantages described above and which does not require that the optical device be readjusted after being moved, for example, between a use position and a rest position.

The present invention achieves the above and other objects, and comprises, briefly, a coupling arrangement of the optical device to a headband in which the optical device is moveable between first and second positions relative to the headband and is automatically locked in at least one of the positions (e.g., a viewing position) whenever it is moved to that position.

According to one embodiment, the head-worn apparatus comprises a headband, an optical device, a support to which the optical device is affixed, means coupling the support to the headband for movement of the support and with it the optical device between a first position and second position relative to the headband, and means for automatically locking the support in either or both of the first and second positions when moved thereto. Further coupling means can be included to affix the optical device to the support which permit adjustment of the optical device relative to the support. Once the further coupling means are adjusted in a given position, e.g., a use position, then the support can be swivelled and returned to that position without having to readjust the optical device on the support.

The locking means can, in various combinations, automatically unlock the support in either or both of the first and second positions by movement of the support toward the other position, and/or prevent unlocking of the support from either or both of the first and second positions by attempted movement of the support. Further, the support can be automatically moved from either or both of the positions to the other position when the support is unlocked.

For example, the support can automatically be unlocked from the first position by movement of the support toward the second position, prevented from unlocking in the second position by attempted movement of the support, and automatically moved from the second position to the first position when the support is unlocked in the second position.

In an embodiment of the head-worn apparatus in which the optical device is a viewing device which in use is positioned in front of the user's eyes, and when not in use swivelled overhead, the coupling means allows the support to move from the overhead, second position to the use, first position automatically by gravity when the support is unlocked in the overhead position.

The coupling means can comprise pivots or bearings permitting relative rotation between the support and the headband and the locking means can comprise a mechanism which locks the support automatically in at least one of the first and second positions without the need to activate or tighten any controls. Arrangement and configuration of locking mechanism structure such as detent pins and detent recesses can provide stops preventing movement of the support beyond the first and second positions and locking/unlocking in the first and/or second position as described above.

According to one embodiment, the support is a generally semi-circular bow having facing but spaced sides or ends which is rotatably connected at its sides (ends) to the headband by the coupling means, e.g., pivots, and the locking means automatically locks the bow in the first position which corresponds to a lower, use position of the optical device and in the second position which corresponds to an upper, rest position of the optical device. In this embodiment, the bow can be unlocked from the rest and use positions simply by moving the bow towards the other position. Alternatively, the locking means can include an operating control, e.g., a knob, which must be activated in order to unlock the bow from either or both of the rest and use positions. The locking mechanism can further include means for adjusting the bow relative to the headband while in the use and/or rest position.

A damping or a braking means, for example, hydraulic, pneumatic or friction, which slows movement of the bow, particularly when lowered, can also be provided. The damping means can permit, for example, a rapid upward and a slow downward swivelling of the bow. Also, a means can be provided for automatically raising the bow when it is unlocked in the lower, use position, in a smooth, jerk-free manner.

Where the optical device includes a light source, a switch for turning the light source on and off can be installed to cooperate with movement of the bow to automatically switch the light source on and off.

The above and other objects, aspects, features and advantages of the present invention will be more readily perceived from the following description of the perferred embodiments thereof taken with the accompanying drawings and appended claims.

BRIEF DESCRIPTION OF THE DRAWINGS

The present invention is illustrated by way of example and not limitation in the figures of the accompanying drawings in which like numbers indicate like parts and in which:

FIG. 4 is a section view of the ophthalmoscope apparatus of FIG. 1 taken along line 4—4 of FIG. 1 depicting an embodiment of a bearing rotatably coupling one end of the support bow of the apparatus to the headband;

FIG. 5 is section view of the ophthalmoscope apparatus of FIG. 1 taken along line 5—5 of FIG. 1 depicting an embodiment of a bearing rotatably coupling the other end of the bow to the headband a the locking mechanism which automatically locks the bow in a rest position and in a use position, and unlocks the bow from the rest position by activation of a control knob;

FIG. 7 is a perspective view of the bearing and locking mechanisms depicted in FIG. 5 shown looking from the inside of the headband with part of the headband broken away;

FIG. 8 is a section view of part of the locking mechanism depicted in FIG. 5 taken along line 8—8 of FIG. 7 showing an alternate embodiment in which the control knob has to be actuated to unlock the bow from the overhead position;

FIG. 9 is a section view similar to that of FIG. 8 depicting another embodiment in which the support bow is unlocked from both the viewing and rest positons by activation of the control knob;

FIGS. 11 and 12 are side views of another embodiment of a head-worn ophthalmoscope apparatus which includes a switch for automatically switching electrical power to the optical unit of the apparatus, FIG. 11 depicting the optical unit in the viewing position with power switched thereto and FIG. 12 depicting the optical unit in the rest position with power switched off.

DESCRIPTION OF THE PREFERRED EMBODIMENTS

Figure 1:
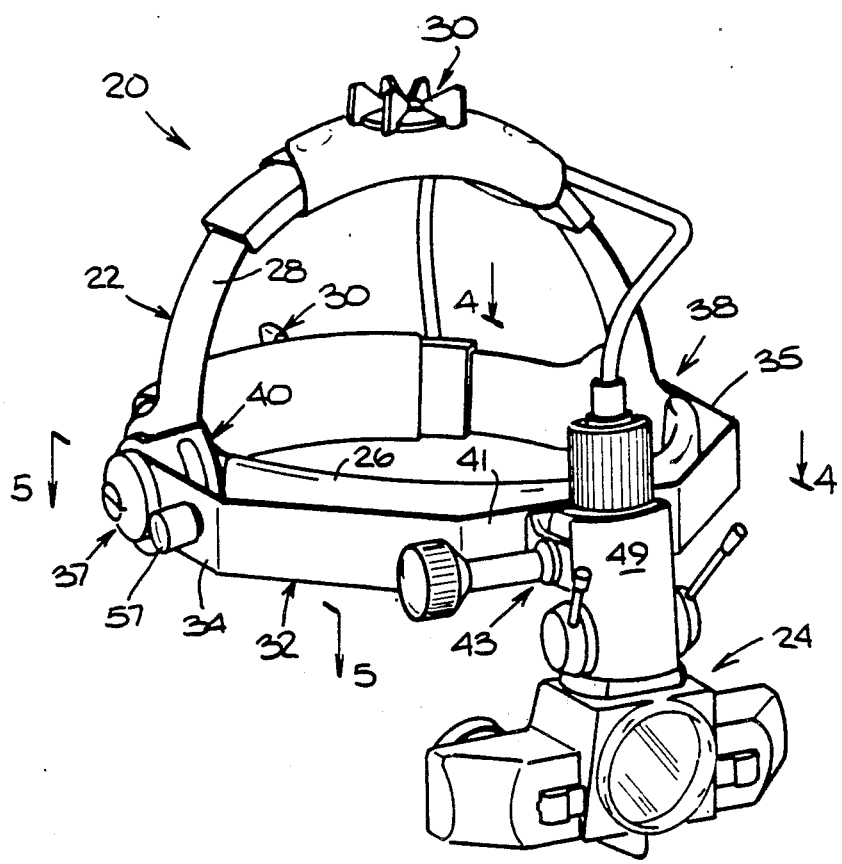
FIG. 1 is a front perspective view of a head-worn ophthalmoscope apparatus according to the invention.
Figure 2:
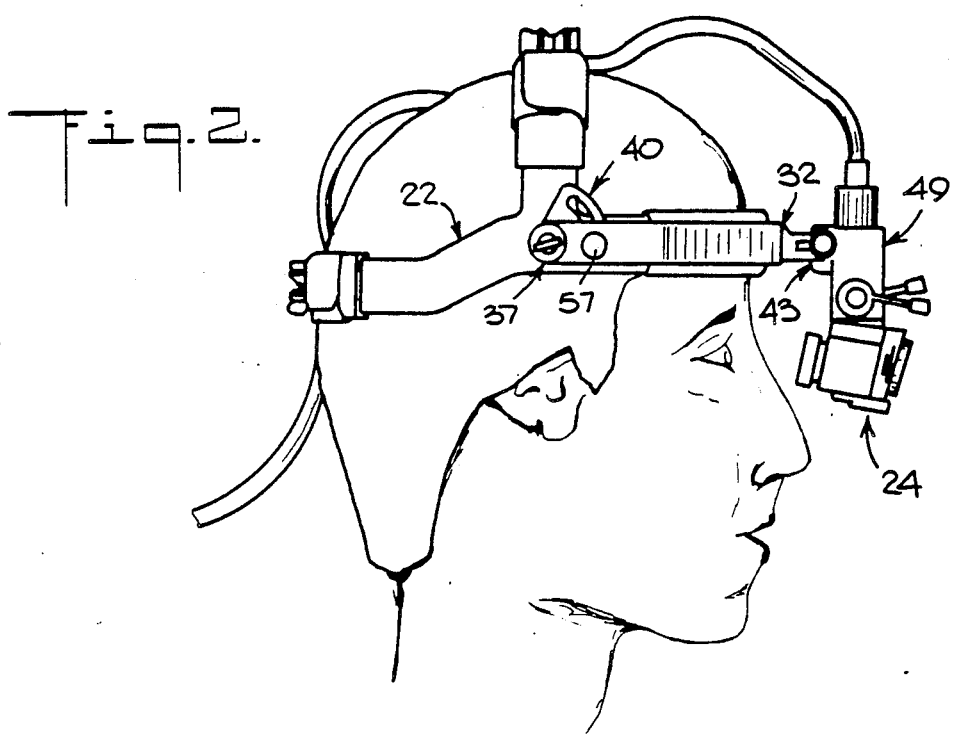
FIG. 2 is a side view of the ophthalmoscope apparatus of FIG. 1 worn on the head of a user with the ophthalmoscope unit disposed in a lower viewing position thereof in front of the user's eyes.

FIG. 1 depicts a head-worn apparatus 20 according to the invention which comprises a headband 22 and an ophthalmoscope unit 24 including a light source, which in the illustrated embodiment is a binocular indirect ophthalmoscope. The headband 22 includes a lower, annular band 26 which encircles the upper part of a user's head as depicted in FIG. 2, and an upper, semicircular band 28 which extends over the top of the user's head. Both the lower band 26 and the upper band 28 can be adjusted by adjusting mechanisms 30 to properly fit a particular user's head. The headband can be made of a flexible material such as plastic.

Figure 3:
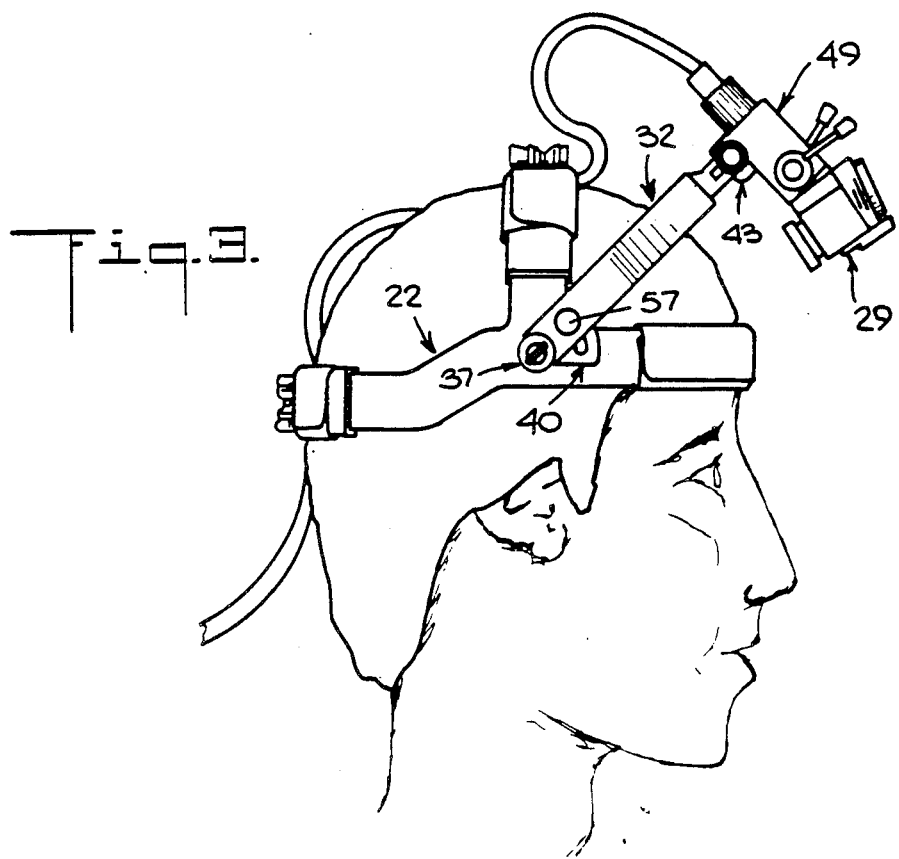
FIG. 3 is a view similar to that of FIG. 2 depicting the ophthalmoscope unit in an overhead, rest position clear of the user's field of vision.
Figure 13:
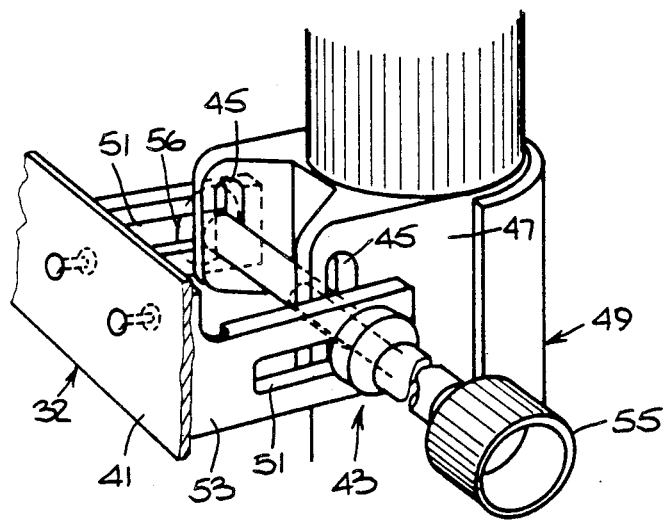
FIG. 13 is a perspective view of part of the ophthalmoscope apparatus of FIG. 1 depicting an articulated mechanism adjustably securing the ophthalmoscope unit to the support bow which is shown broken away.

A support bow 32, preferably made of metal, of generally semi-circular configuration is rotatably coupled at its sides or ends 34, 35 by coupling means 37 and 38. A locking mechanism 40 locks the bow in a first lowered position and in a second raised position as depicted in FIGS. 2 and 3. The ophthalmoscope unit 24 is adjustably connected to the central region 41 of the bow 32 by an articulated mechanism 43. The articulated mechanism 43 (see FIG. 13) is conventional and includes a pair of slots 45 in a bracket 47 affixed to the illumination unit 49 of the ophthalmoscope unit 24 and another pair of slots 51 in a bracket 53 rigidly connected to the central region 41 of the bow 32. The slots 45, 51 extend transversely to each other to permit relative vertical and horizontal adjustment of the ophthalmoscope unit 24 relative to the headband 22. The brackets 47 and 53 are coupled by means a threaded bolt 55 extending through the slots and a nut 56 to which the bolt is threaded. Upon loosening the threaded bolt 55, the ophthalmoscope unit 24 can be displaced and pivoted relative to the bow 32.

Referring next to FIGS. 2 and 3, the ophthalmoscope unit 24 can be adjusted relative to the user's eyes when the bow 32 is in its lower, use or viewing position depicted in FIG. 2 by means of the articulated mechanism 43, as described above. The coupling means 37, 38 and the locking mechanism 40 permit the bow to be swiveled upwardly to the upper, rest postion depicted in FIG. 3. The locking mechanism 40 includes structure which automatically locks the bow 32 in the FIG. 2 viewing position and in the FIG. 3 rest position. This structure prevents movement of the bow downwardly beyond the viewing postion of FIG. 2 and upwardly beyond the rest postion of FIG. 3. Thus, the ophthalmoscope unit 24 can be moved between the viewing and rest positions by pivoting the bow, and the locking mechanism 40 automatically locks the bow when it reaches the FIG. 2 and FIG. 3 positions. The locking mechanism 40 also includes structure which enables the user to unlock the bow from the FIG. 2 viewing position simply by manually raising it without the need to actuate or loosen any control, and structure which requires the user to press the knob 57 to unlock the bow form the FIG. 3 rest position and permit it to be swivelled to the FIG. 2 viewing position under the force of gravity alone, although the user may wish to gently guide the bow in its movement from the rest to the viewing position. Once the position of the ophthalmoscope unit 24 has been adjusted while in the viewing position relative to the user's pupils by a further coupling means in the form of an articulated mechanism 43, the ophthalmoscope unit 24 can be swivelled from the viewing position to the rest position and back without the need to readjust the position of the ophthalmoscope unit since the bow 32 always returns to the same viewing position due to stops in the locking mechanism 40.

Referring to FIG. 4, the coupling means 38 coupling side 35 of the bow 32 to the headband 22 comprises a bearing or pivot pin 58 extending through holes in the bow and headband. The head 59 of the bearing pin 58 seats in a recess 60 in the headband and a nut 61 is threaded to the free end of the pivot pin 58. A washer 62 is disposed between the headband 22 and the bow 32, and a washer 63 is disposed between the bow 32 and the nut 61. The washers are made of a low friction material to facilitate relative rotation between the bow 32 and headband 22 and between the bow 32 and the nut 61. A spring 64 is inserted in a cylindrical recess in the nut 61 and provides a frictional force sufficient to present movement of the bow 32 axially of the pivot pin 58 while permitting the bow 32 to be swivelled.

Figure 6:
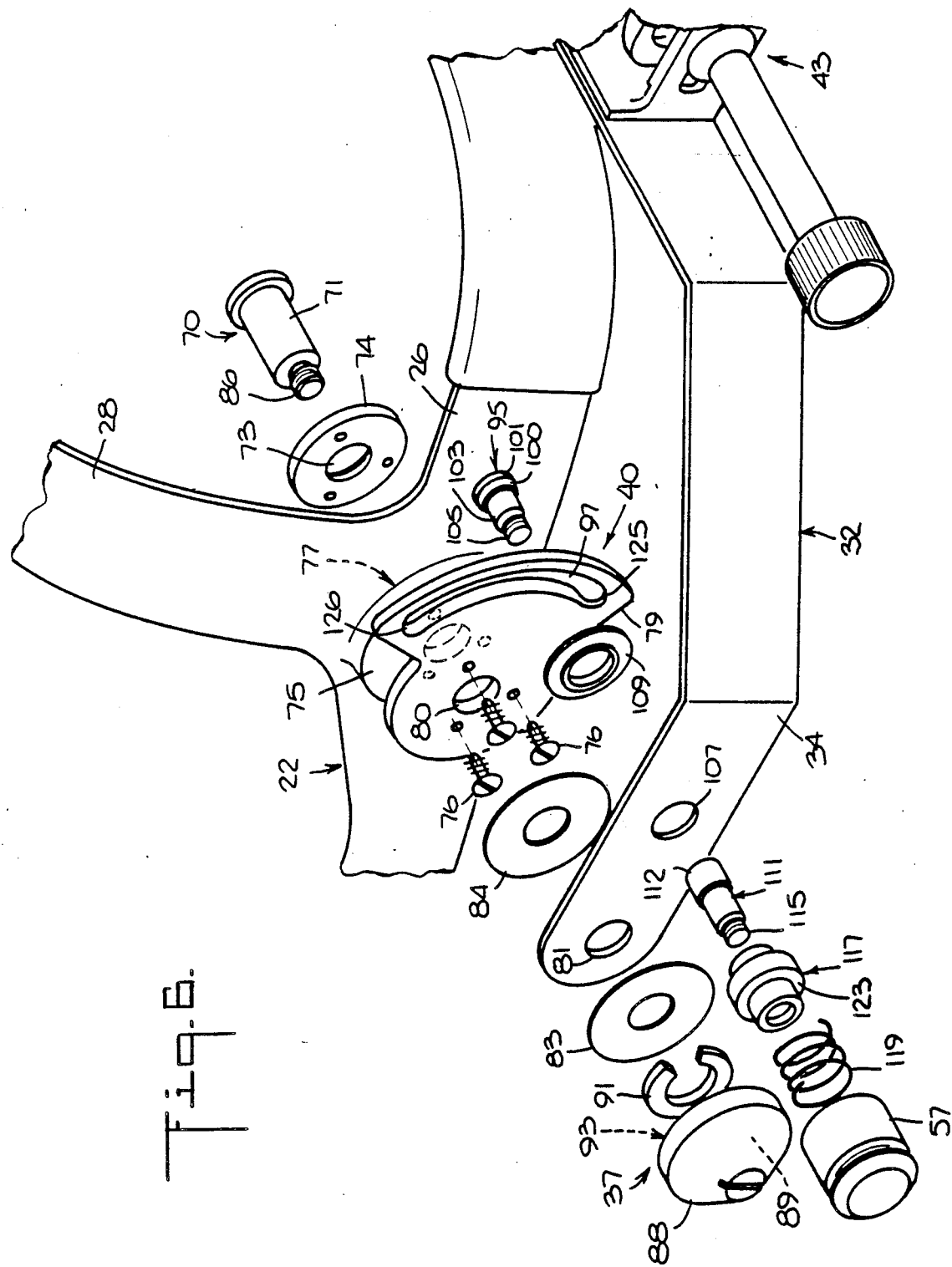
FIG. 6 is an exploded perspective view of a portion of the ophthalmoscope apparatus of FIG. 1 depicting the bearing and locking mechanisms of FIG. 5 coupling the support bow to the headband.

Referring next to FIGS. 5 and 6, the coupling means 37 coupling side 34 of the bow 32 to the headband 22 comprises a bearing or pivot pin 70 having a cylindrical shaft portion 71 extending through a hole 73 in a bearing plate 74 disposed in a circular recess 75 on the inside of the headband 72 and rigidly secured therein by screws 76. The bearing plate 74 forms part of the locking mechanism 40. The headband 22 includes a hole 77 aligned with the hole 73 of the bearing plate 74 through which the shaft 71 of the pivot pin 70 extends. The locking mechanism 40 includes a slotted plate 79 preferably made of metal having a hole 80 aligned with the holes 77, 73 in the headband and bearing plate through which the shaft 71 of the pivot pin extends. The slotted plate 79 is rigidly secured to the headband 22 by the screws 76 which extend through the slotted plate 79 and the headband 22 to the bearing plate 74. The end 34 of the bow 32 also includes a hole 81 aligned with the holes in the slotted plate, headband and bearing plate through which the shaft 71 of the pivot pin also extends. Disposed on each side of the bow 32 are washers 83, 84 through which the pivot pin also extends. The shaft 71 of the pivot pin includes a smaller diameter, threaded portion 86 and the coupling means 37 includes a nut 88 having an internally threaded portion 89 to which the pivot pin is threaded. The coupling means 37 also includes a spring 91 disposed in a cylindrical recess 93 in the knob 88. The washers 83, 84 are made of a low friction material to facilitate relative rotation between the bow 32 and the slotted plate 79 and between the bow 32 and the knob 88. The spring 91 provides a friction force sufficient to prevent movement of the bow 32 axially of the pivot pin 70 while permitting the bow 32 to be swivelled. The coupling means 37 and 38 are thus generally similar and provide for pivoting of bow 32 about a pivot axis extending through pivot pin 70 and about a pivot axis extending through pivot pin 58, respectively.

The locking mechanism 40 in addition to the slotted plate 79 and the bearing plate 74 includes a detent pin 95 which extends through a circularly-shaped slot 97 in the slotted plate 79. The detent pin 95 includes a head having a conical section 100 and a cylindrical section 101, and a shaft 103 ending in a threaded section 105. The detent pin 95 extends through the slot 97 and through a hole 107 in the bow 32. A sleeve 109 is disposed between the slotted plate 79 and the bow 32. A shaft extension 111 having an internal thread on one end 112 is threaded to the threaded portion 105 of the detent pin 95. The shaft extension 111 includes a threaded portion 115 at its other end. A bearing bushing 117 is inserted onto the shaft extension 111 and is axially moveably supported thereon. A compression spring 119 is disposed between the control knob 57 and a flange 123 of the bushing 117. The control knob 57 is threaded to the threaded portion 115 of shaft extension 111. The compression spring 119 pulls the conical section 100 of the detent pin 95 into and against stops 125 and 126 disposed at opposite ends of the slot 97 in the slotted plate 79. In the embodiment depicted in FIGS. 5 and 6, the lower use stop 125 and the overhead rest stop 126 are conically configured as extensions of slot 97 corresponding to the conical section 100 of the detent pin 95. The conical surfaces of the stops 125, 126 cooperate with the conical section 100 of the detent pin 95 as camming surfaces to unseat the conical section 100 of the detent pin 95 from the stops 125, 126 against the force of spring 119 when the bow 32 is moved from one locked position towards the other locked position. If, however, a stop 125a, 126a (see FIGS. 8 and 9) is not conically configured, then the detent pin 95 is not unseated from the stop 125a, 126a by attempted movement of the bow 32. In the embodiments of FIGS. 8 and 9, an inward axial force must be applied to the knob 57 to unseat the detent pin 95 from stops 125a, 126a, and thereby permit the bow 32 to be swivelled. The circumferential length of the slot 97 and the opposed stops 125 and 126 establish the angle over which the bow 32 can be rotated relative to the headband 22, and the stops 125, 126 provide fixed limits for such rotation.

The locking mechanism 40 operates as follows. FIG. 7 shows the bow 32 located in an intermediate position between the stops 125, 126. When the bow 32 is swivelled in the direction of one of the stops 125, 126, the conical section 100 of the detent pin 95 automatically becomes engaged in the associated conically configured stop 125 or 126 as a result of a force applied to the detent pin 95 by the compression spring 119. To unlock or release engagement of the detent pin 95 in either of stops 125, 126, a force is be applied to the bow 32 in a direction to move it towards the opposite stop. The force required to unseat the detent pin 95 is dependant upon the pressure exerted by the compression spring 119 and, of course, on the shape and material of the tapered parts of the detent pin 95 and the slot stops 125, 126. By selecting the compression force and the shape and material of the tapered parts, it is possible to achieve a swivelling operation of the bow 32 in which the bow 32 is automatically locked in the rest and viewing positions depicted in FIGS. 2 and 3 and can be unlocked by simply moving the bow 32 towards the opposite position without requiring any other manipulations by the user.

Referring next to FIG. 8, a slot 97a is provided with a stop 125 identical to the stop 125 in FIGS. 5-7 and a stop 126a which does not include the tapered or conical configuration of stop 126, but rather a cylindrically configured stop having squared walls rather than tapered walls. The cylindrical section 101 of the detent pin 95 fully seats in the cylindrically configured stop 126a so that the detent pin 95 cannot be unseated simply by attempting to move the bow 32 towards the opposite stop 125. Instead, it is necessary to apply an inward axial force to the detent pin 95 to cause its cylindrical portion to be unseated from the cylindrical stop. Thus, to unseat the bow 32 from the rest stop 126a, it is necessary to depress the knob 57. This arrangement ensures that the detent pin 95 will not be unseated from the stop 126a in the overhead rest position of the unit accidently by movements of the user such as nodding.

Referring next to FIG. 9, a slot 97b is depicted having a rest stop 126a identical to the rest stop 126a in FIG. 8 and a use stop 125a which is cylindrically configured and thus is identical to the rest 126a. In the embodiment depicted in FIG. 9, the bow is locked in the rest and use positions and cannot be unlocked by simply attempting to move the bow 32. Rather, the knob 57 must be depressed to unlock the bow 32 in both the rest and the use positions.

Figure 10:
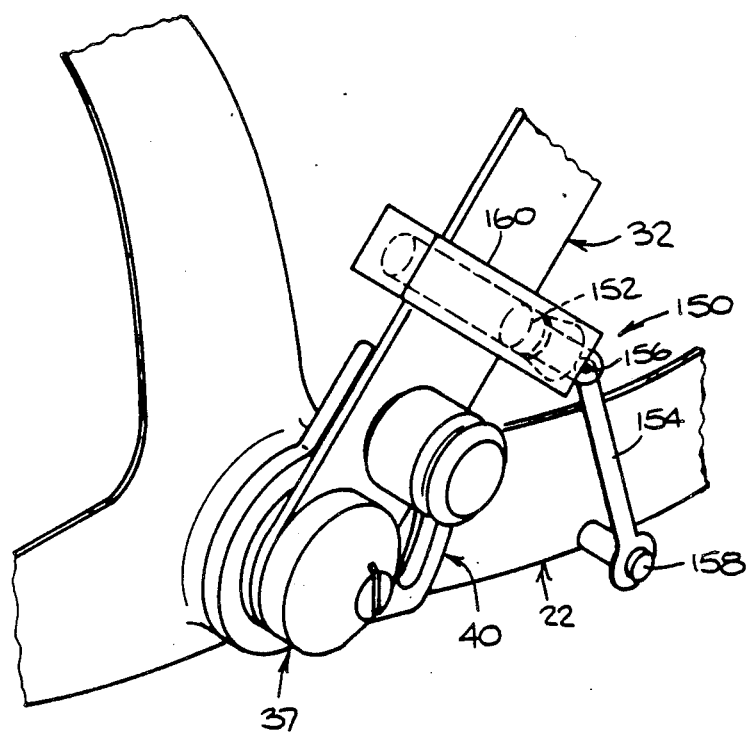
FIG. 10 is a perspective view of part of another embodiment of a head-worn ophthalmoscope apparatus depicting the coupling and locking mechanisms and a braking mechanism for damping swivelling movement of the support bow.

Referring next FIG. 10, an embodiment is depicted which includes a hydraulic or pneumatic damper 150 which damps the motion of the bow 32 in its swivelling movement between the rest and use positions. The damper 150 permits a gradual and automatic swivelling from the upper rest to the lower use position after the bow 32 has been unlocked. The damper 150 is similar to the type used in cassette recorders, where actuation of a release key causes a lid with the cassette inserted therein to gradually and smoothly move between an operating position and a load/unloading position.

The damper 150 includes a piston rod 152 connected to a push rod 154 by means of a pivoted joint 156. The push rod 154 is rotatably secured on a bearing pin 158 secured to the headband 22. The piston rod 152 is moveable in a cylinder 160 secured to the bow 32. The cylinder includes a fluid which damps the motion of the piston rod in the cylinder. When bow 32 is lowered, the push rod 154 causes the piston 152 to move in the cylinder 160. Since the motion of the piston in the cylinder is damped, the motion of the bow 32 relative to the headband 22 is damped. The damper 150 can be of the type which provides damping action in only one direction, so that no force has to be applied to overcome damping in moving the support bow 32 from its use position to its rest position, for example.

Referring next to FIGS. 11 and 12, an embodiment of a head-worn ophthalmoscope apparatus is depicted which includes a switch 180 controlling supply of electrical power to the illumination unit 49, which typically includes a halogen lamp, of the ophthalmoscope unit 24. The switch 180 automatically supplies and interrupts current to the illumination unit 49 in accordance with the position of the bow 32, automatically closing a circuit supplying current to the illumination unit 49 when the bow 32 and ophthalmoscope unit 24 are in the use position (see FIG. 11) and interrupting current to the illumination unit 49 when the bow 32 and the ophthalmoscope unit 24 are in the rest position (FIG. 11). Typically, examiners do not take the trouble to switch the power off to the light source in the illumination unit during pauses in an examination, thus, needlessly using the light source and power from a power source. The switch 180 prolongs the service life of the light source and prevents excessive heating of the illumination unit housing.

The switch 180 includes a housing 182 secured to the bow 32 to which are connected a conductor 184 from a power source (not shown) and a conductor 186 to the light source in the illumination unit. The switch housing 182 encloses a microswitch having a actuator pin 188 projecting from the housing. The headband 22 includes a clip 190 secured thereto in a position to contact and depress the actuator pin 188 of the switch when the bow 32 is lowered to the use position of FIG. 11, thereby switching power to the light source in the illumination unit 49. In FIG. 12, the bow 32 is lifted to a rest position in which the actuator pin 188 fitch interrupts power from the power source to the illumination unit.

A preferred embodiment of a locking mechanism has been illustrated in the drawings and described above. However, other locking mechanisms can be used to accomplish automatic locking of the bow 32 in one or more positions relative to the headband 22. For example, a ratchet mechanism which includes detent structure corresponding to the lock positions can be used. The detent structure can include camming surfaces or squared surfaces for detent pins which enable unlocking simply by movement of the bow or require actuation of a control to unseat the detent pins.

It is possible to employ the described embodiments alone or in any combination. Moreover, use of the headband of the invention is not limited to ophthalmoscope units but can be extended to many head-worn devices, such as binoculars, lupes, headlamps, lupes with headlamps, and for employment in many medical and technical fields.

Certain changes and modifications of the embodiments disclosed herein will be readily apparent to those skilled in the art. It is the applicants' intention to cover by the claims all those changes and modifications which could be made to the embodiment of the invention herein chosen for the purpose of the disclosure without departing from spirit and scope of the invention.

What is claimed is:

1. Head-worn apparatus comprising a headband, a medical optical device, a moveable bow-like support having opposed ends each of which is coupled to the headband and a central region to which the optical device is coupled, means coupling the opposed ends of the support to the headband for pivoting the support and with it the optical device about a pivot axis between a first position relative to the headband and a second position relative to the headband, and means for automatically locking the support in at least one of the first and second positions when moved thereto, the locking means including means coupled to a first end of the support and pivotable with respect to the headband about the pivot axis and means fixed with respect to the headband disposed adjacent the first end of the support, the means pivotable with respect to the headband and the means fixed with respect to the headband cooperating to engage each other and automatically lock the support in the respective position when moved thereto.

2. The head-worn apparatus according to claim 1 wherein the locking means includes means automatically unlocking the support from at least one position by movement of the support when in the one locked position towards the other position.

3. The head-worn apparatus according to claim 1 wherein the locking means includes means preventing unlocking of the support from at least one position by attempted movement of the support.

4. The head-worn apparatus according to claim 1 wherein the locking means locks the support in both positions and includes means automatically unlocking the support from one position by movement of the support when locked in the one position towards the other position and preventing unlocking of the support when locked in the other position by attempted movement of the support.

5. The head-worn apparatus according to claim 1 wherein the coupling means automatically moves the support from at least one locked position to the other position when the support is unlocked from the one locked position.

6. The head-worn apparatus according to claim 1 wherein the locking means automatically locks the support in both the first and the second positions and includes means automatically unlocking the support when in the first locked position by movement of the support towards the second position and means preventing unlocking of the support when in the second locked position by attempted movement of the support, and wherein the coupling means automatically moves the support from the second position to the first position when the support is unlocked from the second position.

7. The head-worn apparatus according to claim 6 wherein the optical device is higher in the second locked position than in the first locked position when the headband is worn by a user, and wherein the coupling means moves the support from the second position to the first position automatically by gravity when the support is unlocked from the second position.

8. The head-worn apparatus according to claim 1 and including further coupling means by which the optical device is coupled to the support, the further coupling means permitting adjustment of the optical device relative to the support.

9. The head-worn apparatus according to claim 1 including damping means damping movement of the support relative to the headband.

10. The head-worn apparatus according to claim 1 wherein the optical device includes a light source and the apparatus includes switch means automatically switching power to the light source and interrupting power to the light source in accordance with the position of the support relative to the headband.

11. Head-worn apparatus comprising a headband, a medical optical device, a bow-like support having opposed ends each of which is coupled to the headband and a central region, first means adjustably coupling the optical device to the central region of the support, second means coupling the ends of the support to the headband for pivoting the support about a pivot axis between a first position relative to the headband and a second position relative to the headband, and locking means for limiting movement of the support between the first and second positions and for automatically locking the support in at least the first position when moved thereto, the locking means including means coupled to a first end of the support and pivotable with respect to the headband about the pivot axis and means fixed with respect to the headband disposed adjacent the first end of the support, the means pivotable with respect to the headband and the means fixed with respect to the headband cooperating to engage each other and automatically lock the support in at least the first position when moved therto, whereby when the headband is worn by a user and the support is in the first position, the optical device can be positioned as desired for use by adjustment of the first means, and thereafter the optical device can be moved out of and back into the first position while the optical device remains adjusted for use.

12. The head-worn apparatus according to claim 11 wherein the locking means includes means automatically unlocking the support from at least one locked position by movement of the support when in the one locked position towards the other position.

13. The head-worn apparatus according to claim 11 wherein the locking means includes means preventing unlocking of the support in at least one locked position by attempted movement of the support.

14. The head-worn apparatus according to claim 11 wherein the locking means automatically locks the support in both the first and second positions and includes means automatically unlocking the support from one of the positions by movement of the support when locked in the one position towards the other position and means preventing unlocking of the support when in the other position by attempted movement of the support.

15. The head-worn apparatus according to claim 11 wherein the second means automatically moves the support from at least one locked position to the other position when the support is unlocked from the one locked position.

16. The head-worn apparatus according to claim 11 wherein the locking means includes means automatically unlocking the support in the first position by movement of the support when in the first position toward the second position and preventing unlocking of the support from the second position by attempted movement of the support, and wherein the second means automatically moves the support from the second position to the first position when the support is unlocked from the second position.

17. The head-worn apparatus according to claim 16 wherein the optical device is higher in the second position than the first position, and wherein the second means moves the support from the second position to the first position automatically by gravity when the support is unlocked from the second position.

18. The head-worn apparatus according to claim 11 wherein the means pivotable with respect to the headband and the means fixed with respect to the headband of the locking means comprise first and second spaced detents and a projection adapted to be engaged in the detents, the detents being fixed to one of the headband and the support and the projection being fixed to the other of the headband and support, the detents and projection being relatively positioned so that the projection engages the first detent in the first position of the support and the projection engages the second detent in the second position of the support, the locking means further comprising means for resiliently urging the projection into the detents to automatically lock the support in at least the first position and means for moving the projection against the urging means out of the detents to unlock the support from at least the first position.

19. The head-worn apparatus according to claim 18 wherein the locking means comprises a configuration of the detents and projection such that the projection cannot move past the first detent in a direction corresponding to movement of the support away from the second position and past the second detent in a direction corresponding to movement of the support away from the first position.

20. The head-worn apparatus according to claim 18 wherein the locking means comprises a camming surface associated with at least one of the detents and the projection includes a cooperating camming surface permitting the projection to ride out of that detent against the urging means when the support is moved to automatically unlock the support.

21. The head-worn apparatus according to claim 18 wherein at least one of the detents is configured to prevent unseating of the projection upon attempted movement of the support and wherein the locking means comprises manually actuable means connected to the projection for withdrawing the projection from a detent to manually unlock the support.

22. The head-worn apparatus according to claim 11 including damping means damping movement of the support relative to the headband.

23. The head-worn apparatus according to claim 11 wherein the optical device includes a light source and the apparatus includes switch means automatically switching power to the light source and interrupting power to the light source in accordance with the position of the support relative to the headband.

24. The head-worn apparatus according to claim 18 wherein the projection comprises a detent pin secured to the headband, the locking means including a member secured to the support having a slot therein through which the detent pin projects, the slot having opposed ends limiting relative movement of the detent pin in the slot and thereby limiting relative movement of the support and the headband between the first and second positions, the opposed ends of the slot being configured as detents.

25. Head-worn apparatus comprising a headband, a medical optical viewing device, a bow-like support having a central region and spaced ends, first means adjustably coupling the optical device to the central region of the support and second means rotatably coupling the support to the headband and including a first pivot rotatably coupling one end of the support to the headband at a first location, a second pivot rotatably coupling the other end of the support to the headband at a second location, and a locking mechanism disposed adjacent at least one of the ends of the support permitting the support to rotate between first and second positions relative to the headband while preventing rotation fo the support beyond the first and second positions and automatically locking the support in at least the first position when moved therto, the locking mechanism including means coupled to a first end of the support and pivotable with respect to the headband and means fixed with respect to the headband disposed adjacent the first end of the support which engage each other and automatically lock the support in at least the first position when moved thereto, the first position corresponding to a use position of the optical device and the second position corresponding to a rest position of the optical device when the headband is worn by a user, whereby, when the headband is worn by a user and the support is in the first, use position, the optical device can be positioned for viewing by a user by adjustment of the first means, and thereafter the optical device can be moved out of and back into the first position while the optical device remains adjusted for viewing.

26. The head-worn apparatus according to claim 25 wherein the means pivotable with respect to the headband and the means fixed with respect to the headband of the locking mechanism comprise first and second spaced detents and a projection adapted to be engaged in the detents, the detents being fixed to one of the headband and the support and the projection being fixed to the other of the headband and support, the detents and projection being relatively positioned so that the projection engages the first detent in the first position of the support and the projection engages the second detent in the second position of the support, the locking mechanism further comprising means for resiliently urging the projection into the detents to automatically lock the support in the first and second positions and means for moving the projection against the urging means out of the detents to unlock the support from the first and second positions.

27. The head-worn apparatus according to claim 26 wherein the locking mechanism comprises a configuration of the detents and projection such that the projection cannot move past the first detent in a direction corresponding to movement of the support away from the second position and past the second detent in a direction corresponding to movement of the support away from the first position.

28. The head-worn apparatus according to claim 27 wherein the locking mechanism includes a camming surface associated with at least one of the detents permitting the projection to ride out of that detent against the urging means when the support is moved towards the other detent to automatically unlock the support.

29. The head-worn apparatus according to claim 27 wherein at least one of detents is configured to prevent unseating of the projection therefrom upon attempted movement of the projection and the locking mechanism comprises manually actuable means connected to the projection for withdrawing the projection from a detent to manually unlock the support.

30. The head-worn apparatus according to claim 25 including damping means damping movement of the support relative to the headband.

31. The head-worn apparatus according to claim 25 wherein the optical device includes a light source and the apparatus includes switch means automatically switching power to the Y
light source and interrupting power to the light source in accordance with the position of the support relative to the headband.

32. The head-worn apparatus according to claim 26 wherein the projection comprises a detent pin secured to the headband, the locking mechanism including a member secured to the support having a slot therein through which the detent pin projects, the slot having opposed ends limiting relative movement of the detent pin in the slot and thereby limiting relative movement of the support and the headband between the first and second positions, the opposed ends of the slot being configured as detents.

33. The head-worn apparatus according to claim 32 wherein the ends of the slots are configured as detents, a first slot end which corresponds to the first position of the support having a camming surface and the detent pin having a camming surface which cooperate to unseat the detent pin from the first slot end upon movement of the support towards the other slot end, and a second slot end which corresponds to the second position of the support having a configuration which prevents unseating of the detent pin upon attempted movement of the support, the locking mechanism including manually actuable means connected to the detent pin for withdrawing it from the second slot end to manually unlock the support.

* * * * *